US 6,693,425 B2

(12) United States Patent
Wache

(10) Patent No.: US 6,693,425 B2
(45) Date of Patent: Feb. 17, 2004

(54) SENSOR HAVING AN ELECTRIC COIL AND GIANT MAGNETORESISTOR FOR DETECTING DEFECTS IN A COMPONENT

(75) Inventor: Gilbert Wache, Avilly St-Leonard (FR)

(73) Assignee: Cegelec, Rueil-Malmaison (FR)

( * ) Notice: Subject to any disclaimer, the term of this patent is extended or adjusted under 35 U.S.C. 154(b) by 0 days.

(21) Appl. No.: 10/268,705

(22) Filed: Oct. 11, 2002

(65) Prior Publication Data

US 2003/0080735 A1 May 1, 2003

(30) Foreign Application Priority Data

Oct. 29, 2001 (FR) .............................. 01 13992

(51) Int. Cl.[7] .................... G01N 27/72; G01N 27/90
(52) U.S. Cl. ...................... 324/235; 324/228
(58) Field of Search ................ 324/228, 232, 324/235, 239–243, 202, 207.2, 207.21, 252

(56) References Cited

U.S. PATENT DOCUMENTS

| 4,829,248 | A | * | 5/1989 | Loubier .................. 324/202 X |
| 5,321,355 | A | * | 6/1994 | Luetzow ................. 324/207.2 |
| 5,500,589 | A | * | 3/1996 | Sumcad ..................... 324/202 |
| 6,150,809 | A | | 11/2000 | Tiernan et al. |
| 6,310,475 | B1 | * | 10/2001 | Kawase et al. ............. 324/235 |
| 6,504,363 | B1 | * | 1/2003 | Dogaru et al. ............. 324/235 |
| 6,583,617 | B2 | * | 6/2003 | LeVert et al. .............. 324/235 |

FOREIGN PATENT DOCUMENTS

| FR | 2 675 261 A | 10/1992 |
| WO | WO 00 60343 A | 10/2000 |
| WO | WO 01 67085 A1 | 9/2001 |

* cited by examiner

Primary Examiner—Gerard R. Strecker
(74) Attorney, Agent, or Firm—Sughrue Mion, PLLC

(57) ABSTRACT

A sensor for detecting defects in a component includes an electric coil fed with a varying electrical current to create a varying magnetic field penetrating at least partly into the component under test, and a defect detector including a magnetoresistor. The above components are accommodated in a protective housing having a detection face disposed near and parallel to a surface of the component under test. The coil has its axis Δ perpendicular to the detection face and the magnetoresistor is in the vicinity of the detection face. The magnetoresistor is a giant magnetoresistor and is disposed so that its sensitivity axis Δ1 sensitive to variations in a magnetic field is parallel to the detection face of the housing. The sensor further includes a first permanent magnet disposed so that it magnetically biases the magnetoresistor in the direction of its sensitive axis Δ1 to a value such that the operating point is a point on a curve, representing the output signal of the magnetoresistor as a function of the value of the component of the magnetic field in the direction of the sensitive axis, which is situated in the vicinity of the middle of a substantially rectilinear portion of the curve.

9 Claims, 4 Drawing Sheets

SENSOR HAVING AN ELECTRIC COIL AND GIANT MAGNETORESISTOR FOR DETECTING DEFECTS IN A COMPONENT

BACKGROUND OF THE INVENTION

1. Field of the Invention

The present invention relates to a sensor for detecting defects in a component.

The component to be tested can be electrically conductive and ferromagnetic or non-ferromagnetic, and in this case the invention can detect defects such as surface or internal cracks.

The invention applies equally to detecting electrically conductive ferromagnetic or non-ferromagnetic particles in a material that is not electrically conductive.

2. Description of the Prior Art

Various techniques for non-destructive testing of metal components are known in the art: for example, Eddy current testing by measuring the impedance of sensing coils, or testing ferromagnetic materials by the dispersion flux method using magnetoresistive sensors. The document EP 0 736 173 B 1 describes, a sensor including an excitation coil whose axis is perpendicular to the surface of the product under test and which is fed with a varying electrical current to generate Eddy currents in the product.

The detector means include two Eddy current detector coils mounted in opposition and two magnetoresistors disposed parallel to each other and connected in a differential circuit. The Eddy current detector coils are coaxial with and inside the excitation coil and the magnetoresistors are parallel to the axial direction of the coils. The detector coils and the magnetoresistors are connected to processor means that include a multichannel processor circuit.

An object of the present invention is to propose a different sensor arrangement offering very high sensitivity.

SUMMARY OF THE INVENTION

The invention therefore provides a sensor for detecting defects in a component, the sensor including an electric coil fed with a varying electrical current to create a varying magnetic field penetrating at least partly into the component under test, and defect detector means including a giant magnetoresistor, the above components being accommodated in a protective housing having a detection face adapted to be disposed near and parallel to a surface of the component under test, the coil having its axis Δ perpendicular to the detection face, and the giant magnetoresistor being situated in the vicinity of the detection face and disposed so that its sensitivity axis Δ1 sensitive to variations in a magnetic field is parallel to the detection face of the housing, which sensor further includes a first permanent magnet disposed so that it magnetically biases the giant magnetoresistor in the direction of its sensitive axis Δ1 to a value such that the operating point is a point on a curve, representing the output signal of the giant magnetoresistor as a function of the value of the component of the magnetic field in the direction of the sensitive axis, which is situated in the vicinity of the middle of a substantially rectilinear portion of the curve.

If the component under test is made of a ferromagnetic material, the sensor advantageously further includes a second permanent magnet associated with an open magnetic circuit having two end surfaces of opposite polarity and situated against the detection face and on diametrically opposite sides of the electrical coil.

One embodiment of the invention will now be described with reference to the accompanying drawings.

DETAILED DESCRIPTION OF THE PREFERRED EMBODIMENT

Figure 1:
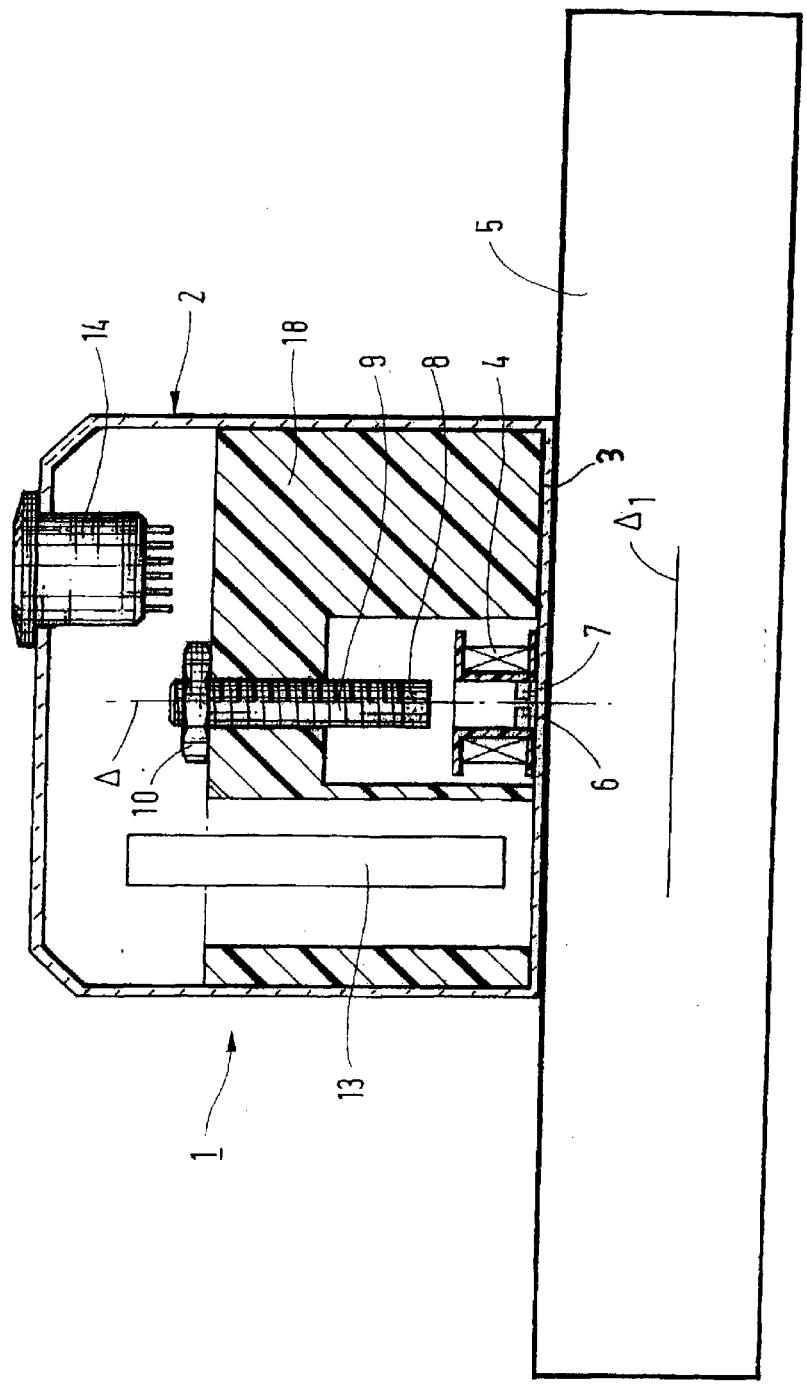
FIG. 1 shows a sensor in accordance with the invention which is particularly suitable for testing amagnetic material components.

Referring to FIG. 1, which shows a sensor 1 according to the invention, a housing 2 that is made of a material that is not electrically conductive and has a bottom face 3 referred to as the detector face contains an electrical coil 4 whose axis Δ is perpendicular to the detection face 3.

The coil 4 is fed with a varying electrical current to create a varying magnetic field penetrating at least partly into the component 5 under test, along which the sensor 1 is moved.

Two giant magnetoresistors (GMR) 6 and 7 are located near the detection face 3, inside the coil 4 and close to its bottom end.

A GMR is a directional component that is sensitive only to the component of the magnetic field in the direction of its sensitivity axis. A GMR is very sensitive to variations in the field in that direction.

The GMR 6 and 7 are disposed side by side so that their sensitivity axes are parallel to the detection face 3. The direction of the sensitivity axis is represented by the line Δ1.

A single GMR could be used, but using two and associating them in a differential circuit eliminates causes of errors due to spurious field variations at the location of the GMR when the sensor moves along the component 5. For example, this eliminates most of the effect of the terrestrial magnetic field that would otherwise cause a measurement error if the path of the sensor were not rectilinear, for example.

Figure 4:
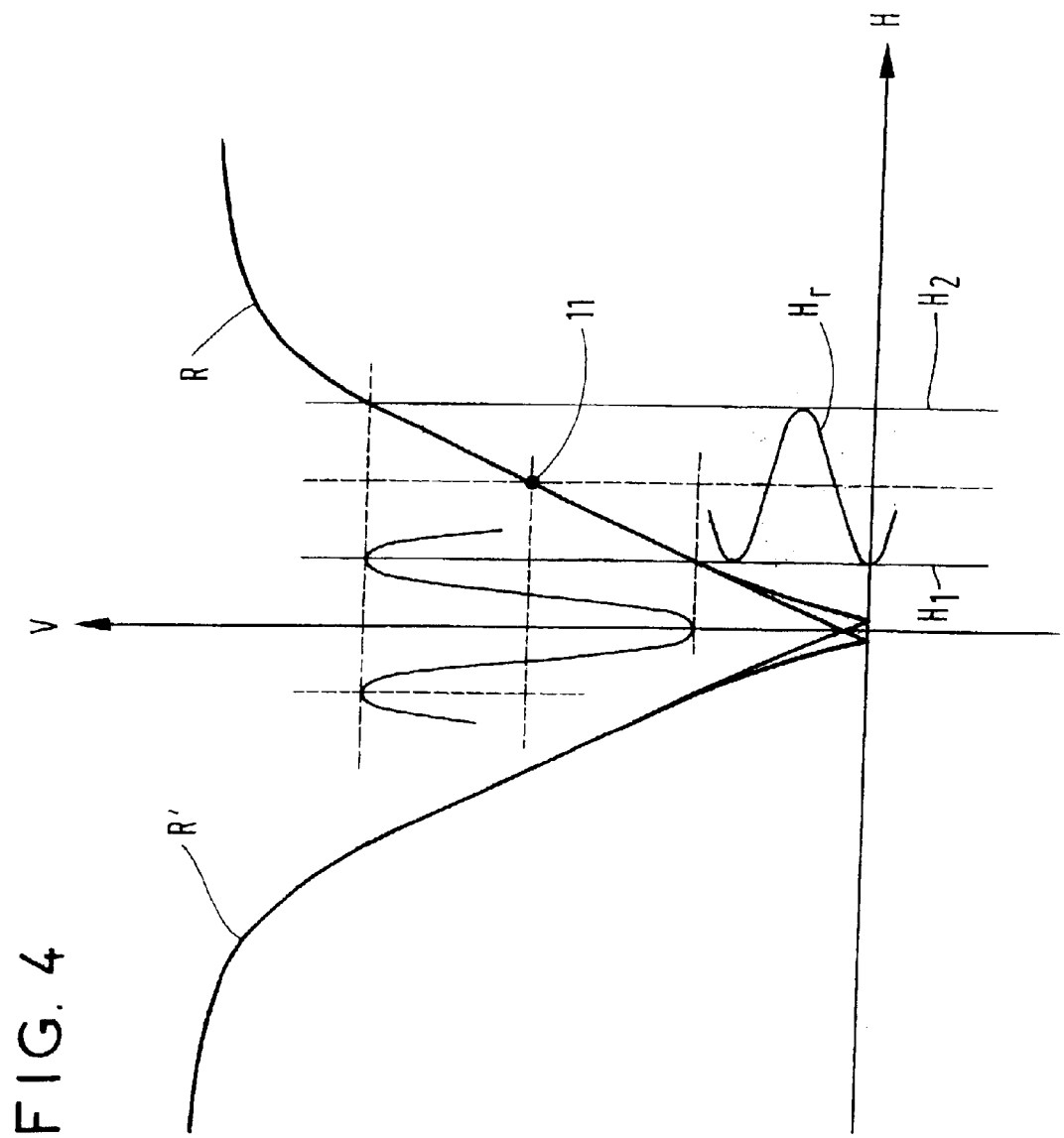
FIG. 4 is a curve of the output voltage V of a giant magnetoresistor as a function of the value H of the component of the magnetic field at the location of the magnetoresistor and in the direction of the sensitivity axis of the magnetoresistor, and the operating point on that curve.

FIG. 4 shows the response curve R, R' of the output voltage V of a GMR as a function of the value of the field H surrounding it (only the value of the component of the field H in the direction of the sensitivity axis of the GMR is considered). As this figure shows, the curve is symmetrical with respect to the ordinate axis V, i.e. the response is positive regardless of the direction of the field along the sensitivity axis.

Referring again to FIG. 1, the sensor further includes a permanent magnet 8 disposed above the coil 4, i.e. on the other side of the coil relative to its face placed against the detection face 3.

It is placed on the axis of the coil at the end of a threaded rod 9 which screws into a non-conductive and amagnetic support 18 with a screwthreaded hole through it enabling the position of the magnet along the axis Δ of the coil to be adjusted. A nut 10 locks the rod in the adjusted position.

The position of the magnet 8 is adjusted so that, at the location of the GMR 6 and 7, it magnetically biases the sensitive axis Δ1 of the GMR to a value such that the operating point is at a point 11 on the curve R in FIG. 4 in the vicinity of the middle of the substantially rectilinear portion of the curve.

Thus, in the absence of defects in the component 5, the resultant field Hr in the direction of the sensitivity axis Δ1 oscillates between two values $H_1$ and $H_2$ corresponding to a rectilinear part of the curve R and situated outside the bottom area, in which there is hysteresis, and before saturation occurs.

The sensor 1 also accommodates a printed circuit card 13 carrying the components of the differential circuit including the GMR 6 and 7, together with the necessary matching circuit. A connector 14 connects this card to the power supply of the coil 4 and the GMR 6 and 7.

Figure 3:
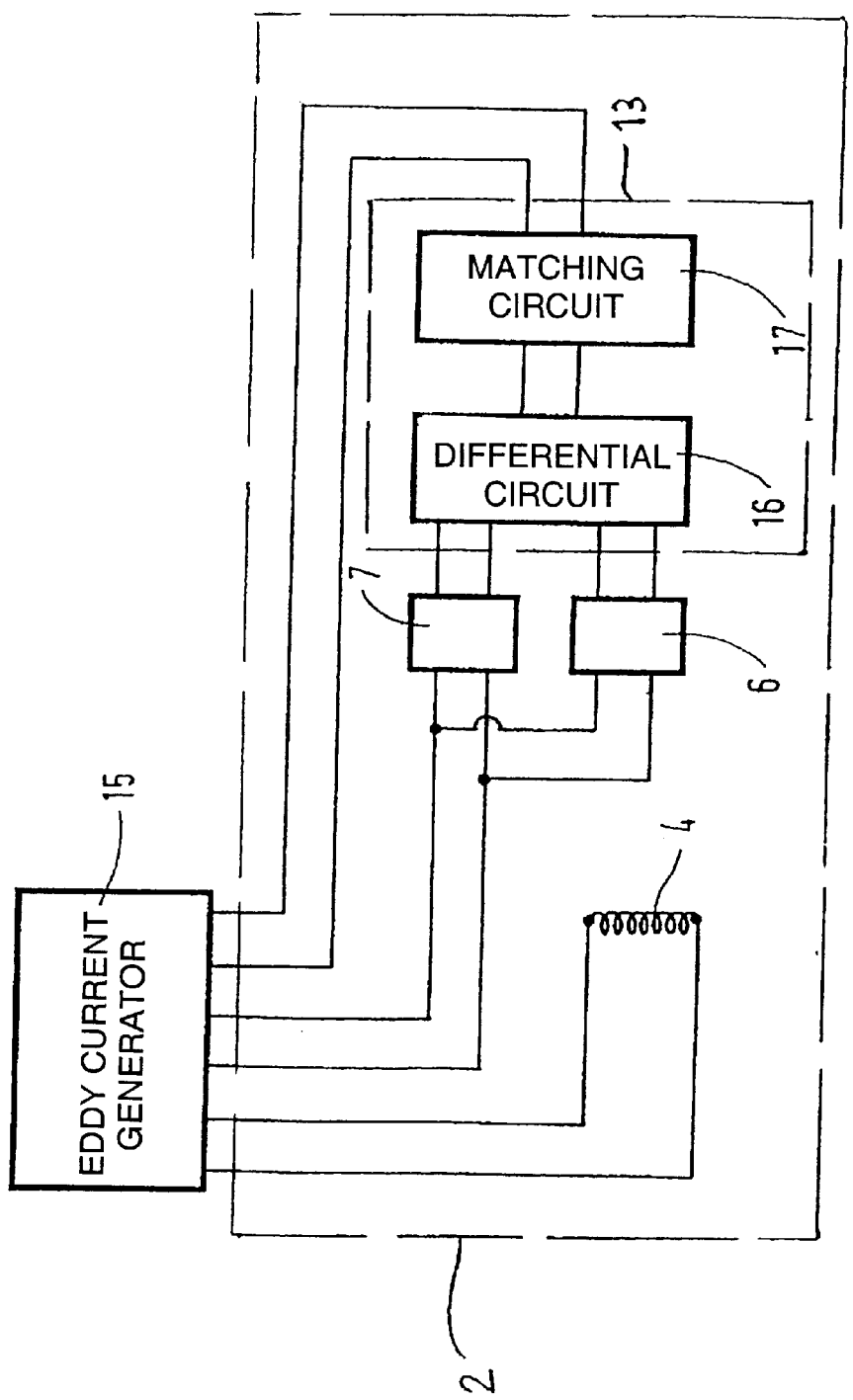
FIG. 3 is a very simplified functional block diagram of a device for detecting defects.

The connector 14 is also connected to an Eddy current generator 15 (FIG. 3) which supplies the coil 4 and the GMR 6 and 7 and processes the output signal of the differential circuit 16 of the GMR and the matching circuits 17 on the printed circuit card 13.

The sensor shown in FIG. 1 is particularly suitable for testing non-ferromagnetic conductive material components 5.

The coil 4, energized with a varying current, induces in the component 5 Eddy currents which in turn produce a varying magnetic field, which generates a resultant field Hr at the location of the GMR (Hr is the component of the field in the direction of the sensitive axis Δ1 of the GMR).

If the sensor encounters a defect such as a crack, the Eddy currents are diverted and this modifies the field produced by those currents and therefore the resultant field Hr, which modification is therefore detected.

The Eddy current generator 15 can modify the excitation frequency of the coil 4 to scan for defects at varying depths in the component 5.

The sensor can equally well be used to detect ferromagnetic or non-ferromagnetic conductive particles in a non-conductive component 5: when the sensor passes over such particles, the resultant magnetic field Hr is modified and this is detected.

Figure 2:
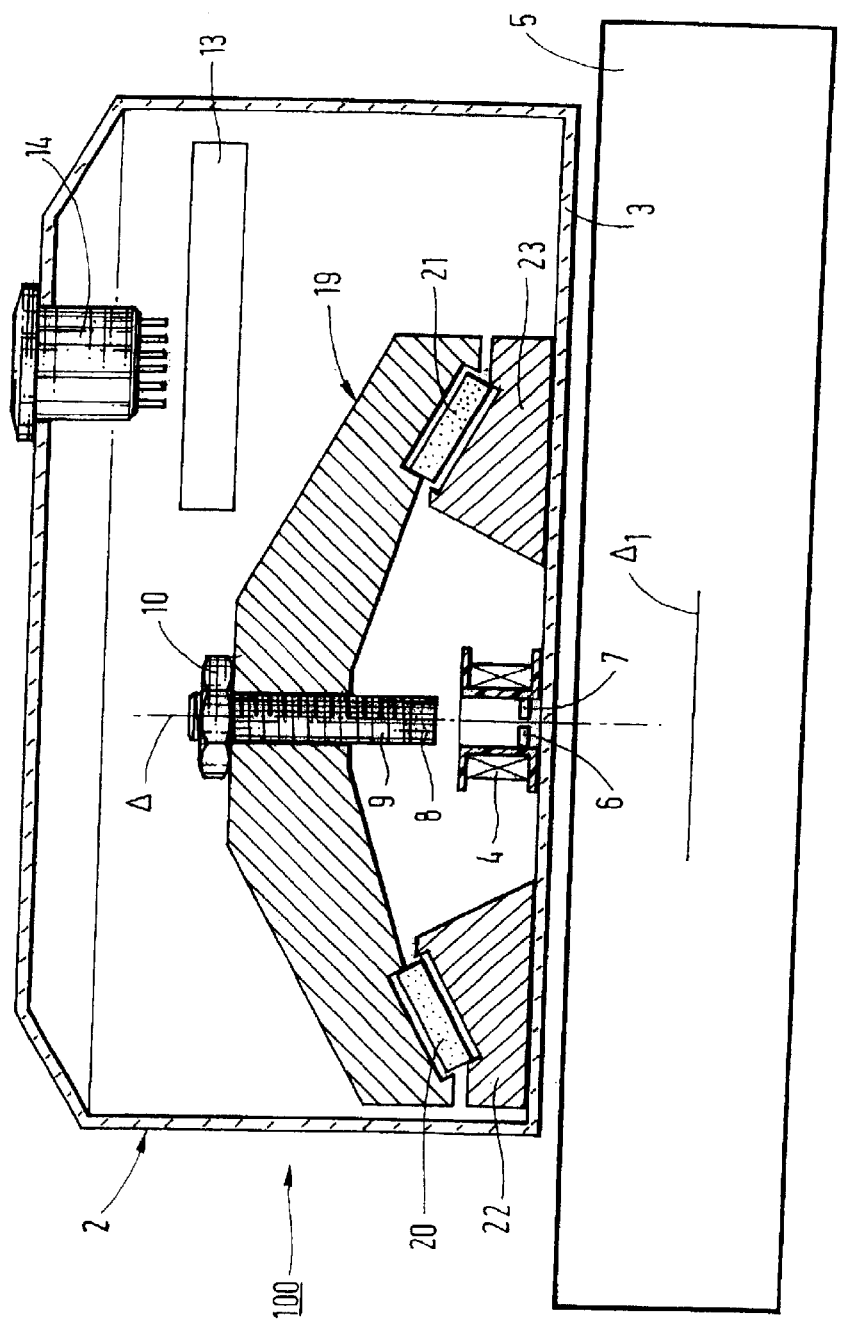
FIG. 2 shows a sensor according to the invention that is particularly suitable for testing ferromagnetic material components.

FIG. 2 shows a sensor according to the invention which is particularly suitable for identifying defects in ferromagnetic material components 5.

To this end, in addition to the excitation coil 4 and the permanent magnet 8 for biasing the GMR 6 and 7, as in FIG. 1, the sensor 100 further includes means for locally magnetizing the component 5 under test so that all the zones scanned by the sensor 100 have a constant relative magnetic permeability $\mu r$ such that visible defects caused in fact by lack of magnetic homogeneity of the component 5 are not detected.

To be able to detect defects deep inside the component, it is desirable to magnetize the component 5 relatively strongly, to obtain a permeability $\mu r$ close to 1.

To do this, the support 18 of the sensor 1 is replaced by an open magnetic circuit 19 including at least one permanent magnet; in FIG. 2 there are two permanent magnets 20 and 21.

The magnetic circuit 19 includes two polepieces 22 and 23 whose end surfaces of opposite polarity are situated against the detection surface 3, on diametrally opposite sides of the coil 4 in the direction of the axis Δ1.

As a general rule, the magnetic circuit is disposed so that the field lines extending from one polepiece to the other all pass into the component 5 without passing through the GMR 6 and 7.

The magnetic circuit 19 is also used as a support for the magnet 8 and its threaded support rod 9 screwed a greater or lesser distance into a screwthreaded hole in the magnetic circuit 19. The locking nut 10 is also shown. As in FIG. 1, there is a printed circuit card 13 carrying the circuits 16 and 17 from FIG. 3, providing the same functions, and the connector 14.

As in FIG. 1, in the event of defects, such as a crack, in the ferromagnetic component 5 from FIG. 2, the Eddy currents produced in the component 5 by the coil 4 are diverted and produce a different induced field, modifying the resultant field Hr at the location of the GMR 6 and 7.

What is claimed is:

1. A sensor for detecting defects in a component, said sensor comprising:

an electric coil fed with a varying electrical current to create a varying magnetic field penetrating at least partly into said component under test; and a defect detector means comprising a giant magnetoresistor, wherein:

said components are accommodated in a protective housing having a detection face adapted to be disposed near and parallel to a surface of said component under test;

said coil has its axis A perpendicular to said detection face;

said magnetoresistor is situated in the vicinity of said detection face and is disposed so that its sensitivity axis Al sensitive to variations in a magnetic field is parallel to said detection face of said housing, and said sensor further comprises a first permanent magnet disposed so that it magnetically biases said giant magnetoresistor in the direction of its sensitive axis Al to a value such that the operating point is a point on a curve, representing the output signal of said giant magnetoresistor as a function of the value of the component of said magnetic field in the direction of said sensitive axis, which is situated in the vicinity of the middle of a substantially rectilinear portion of said curve.

2. The sensor claimed in claim 1, for detecting defects in a ferromagnetic component, further comprising a second permanent magnet associated with an open magnetic circuit having two end surfaces of opposite polarity and situated against said detection face and on diametrally opposite sides of said electrical coil.

3. The sensor claimed in claim 1, comprising two giant magnetoresistors in a differential circuit.

4. The sensor claimed in claim 1, wherein said first permanent magnet is situated over said electrical coil, on the opposite side of said coil relative to its face situated against said detection face, and said sensor comprises means for adjusting its position along the axis of said coil.

5. The sensor claimed in claim 4, wherein said means for adjusting the position of the first permanent magnet along the axis of said coil comprises a threaded rod connected to said first permanent magnet, said threaded rod being arranged in a non-conductive support.

6. The sensor claimed in claim 2, wherein:

said first permanent magnet is situated over said electrical coil, on the opposite side of said coil relative to its face situated against said detection face, and said sensor comprises means for adjusting its position along the axis of said coil; and said means for adjusting the position of the first permanent magnet along the axis of said coil comprises a threaded rod connected to said first permanent magnet, said threaded rod being arranged in said open magnetic circuit.

7. The sensor claimed in claim 1, wherein said first permanent magnet is arranged above said giant magnetoresistor on a side opposite to said detection face.

8. The sensor claimed in claim 3, further comprising a printed circuit card comprising components of said differential circuit.

9. The sensor claimed in claim 1, further comprising a connector arranged on said protective housing that connects said sensor to a power supply.

* * * * *